United States Patent
Gilmore et al.

(10) Patent No.: US 7,569,839 B2
(45) Date of Patent: Aug. 4, 2009

(54) METHOD FOR CLASSIFICATION OF CARBON NANOTUBES AND OTHER MATERIALS

(75) Inventors: Adam M. Gilmore, Flemington, NJ (US); James R. Mattheis, East Brunswick, NJ (US)

(73) Assignee: Jobin Yvon, Inc., Edison, NJ (US)

( * ) Notice: Subject to any disclaimer, the term of this patent is extended or adjusted under 35 U.S.C. 154(b) by 14 days.

(21) Appl. No.: 11/113,961

(22) Filed: Apr. 25, 2005

(65) Prior Publication Data

US 2006/0241872 A1      Oct. 26, 2006

(51) Int. Cl.
G01N 21/64        (2006.01)
(52) U.S. Cl. .................... 250/459.1; 356/951
(58) Field of Classification Search ............... 356/951; 250/459.1
See application file for complete search history.

(56) References Cited

U.S. PATENT DOCUMENTS

| | | | | |
|---|---|---|---|---|
| 4,031,398 | A * | 6/1977 | Callis et al. ............. 250/458.1 |
| 4,365,303 | A * | 12/1982 | Hannah et al. ............. 702/28 |
| 5,049,738 | A | 9/1991 | Gergely et al. ............. 250/301 |
| 5,308,982 | A * | 5/1994 | Ivaldi et al. ............. 250/339.12 |
| 6,280,677 | B1 | 8/2001 | Yakobson |
| 6,571,118 | B1 * | 5/2003 | Utzinger et al. ............. 600/476 |
| 6,669,918 | B2 | 12/2003 | Schleier-Smith |
| 6,687,000 | B1 * | 2/2004 | White ..................... 356/328 |
| 6,720,553 | B2 | 4/2004 | Bonnell |
| 6,752,977 | B2 | 6/2004 | Smalley |
| 6,774,333 | B2 | 8/2004 | Hannah |
| 6,777,960 | B2 | 8/2004 | Unger |
| 6,863,943 | B2 | 3/2005 | Wang |
| 7,072,770 | B1 * | 7/2006 | Schweitzer et al. ........... 702/25 |
| 2003/0031619 | A1 | 2/2003 | Schleier-Smith |
| 2003/0124717 | A1 | 7/2003 | Awano et al. |
| 2003/0168385 | A1 | 9/2003 | Papadimitrakopoulos |
| 2003/0183560 | A1 | 10/2003 | Hannah |
| 2004/0038556 | A1 | 2/2004 | French |
| 2004/0040834 | A1 * | 3/2004 | Smalley et al. ............. 204/164 |
| 2004/0084353 | A1 | 5/2004 | Hannah |
| 2004/0120880 | A1 | 6/2004 | Zhang |
| 2004/0200817 | A1 | 10/2004 | Hannah |

* cited by examiner

*Primary Examiner*—David P Porta
*Assistant Examiner*—Jessica L Eley

(57) ABSTRACT

A method for identification of a sample of a material is disclosed. The method includes illuminating a sample at a plurality of excitation wavelengths, measuring the intensity at each of the plurality of excitation wavelengths, locating the values of maxima in the three-dimensional intensity contour, comparing the maxima to a library of values of known maxima associated with known species, generating a model of a three-dimensional intensity contour based on maxima values comprising values of likely maxima from the library, comparing the model of an intensity contour to the measured contour to determine residual errors, outputting the species associated with the maxima values used to generate the model as an indicator of species, determining corrections to the model of a three-dimensional intensity contour to generate a corrected model, and returning to the comparison step to test the corrected model.

7 Claims, 5 Drawing Sheets

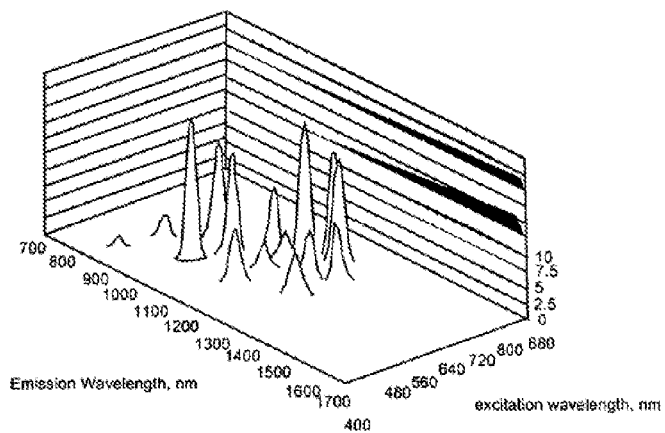
Figure 4
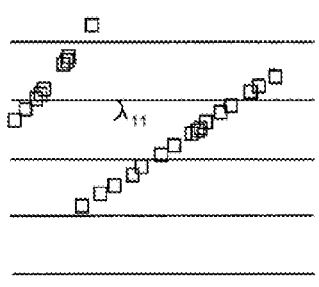
Figure 5
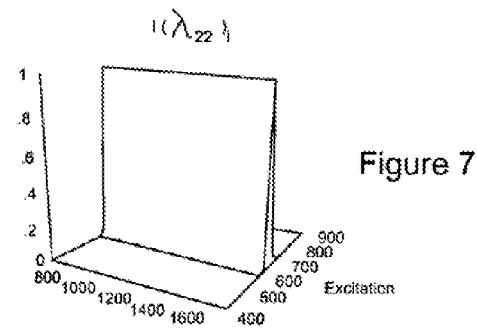
Figure 7
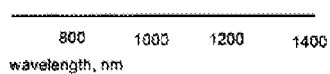
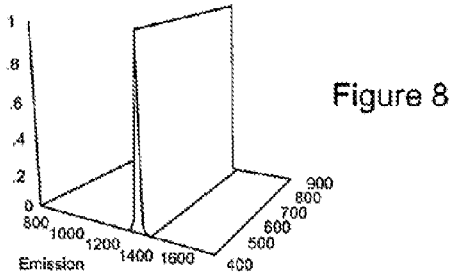
Figure 8
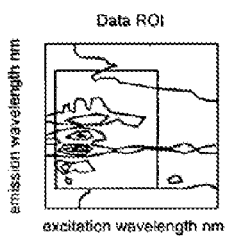
Figure 10
Figure 9
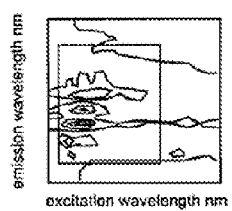
Figure 11

METHOD FOR CLASSIFICATION OF CARBON NANOTUBES AND OTHER MATERIALS

TECHNICAL FIELD

The present invention relates to the field of optical analysis of materials, particularly semiconducting single-walled carbon nanotubes (SWCNT) through the use of luminescence spectroscopy.

BACKGROUND ART

A theory for the relationship between the fundamental single-walled carbon nanotube structure parameters (diameter and chirality) and the optical transitions of absorbance and emission (photoluminescence) of light energy is known from the work of Weismann and coworkers (see e.g. Bachilo et al. (2002) Science 298:2361-2366).

SWCNTs are formed by a vectorial wrapping of a sheet of graphite crystal into a cylinder. The parameters defining the direction of the wrapping vector comprise what is known as the zigzag axis and the armchair axis, where the potential 'chirality' angle of the 'wrapping vector' is constrained between 0 degrees and 30 degrees between the two axes. The diameter of the tube is defined by the length of the wrapping vector and the chirality angle. The graphite sheet is mapped with two integer parameters, n and m, which plot the coordinates from n,m having the values (0,0) (the coordinate at the origin of the wrapping vector) to n,m having the values (x,y), where x and y are the coordinates marking the terminus of the wrapping vector. As alluded to above, the angle defined from (0,0) to (x,y) is defined as the chirality angle. Hence, a carbon nanotube can be equivalently described by its diameter ($d_t$) or by its chirality angle and terminal (n,m)=(x,y) values.

Bachilo et al., above, disclose a mathematical relationship between the size and chirality of a given nanotube species and the energy values for both the absorption and emission optical transitions. Bachilo et al. define equation systems used to describe the observed relationships between the SWCNT diameter parameter ($d_t$) and two key optical transition parameters, namely 1) the semiconductor absorption or upward transition of electrons from the valence band 2 to conductance band 2, i.e. the energy of a photon which drives an electron across the bandgap when it is excited, and 2) the subsequent emission transition of electrons from the conductance band 1 to the valence band 1, i.e. the energy of a photon emitted by the carbon atom when an electron in the conductance band 1 returns across the bandgap to the valance band 1.

Essentially, the simplest, theoretical relationships can be viewed as quasi-linear according to the following equations:

$$d_t = \lambda_{22} 4 a_{cc} \gamma_o / hc = \lambda_{11} 2 a_{cc} \gamma_o / hc$$

Where, $\lambda_{22}$ is the photon energy needed to drive the electron in the transition from v2 to c2 and $\lambda_{11}$ is the energy of the photon emitted during the transition from c1 to v1, $a_{cc}$ is the C—C bond distance and $\gamma_o$ is the interaction energy between neighboring carbons, h is Planck's constant and c is the speed of light.

Bachilo et al (2002) used a HORIBA Jobin Yvon Fluorolog spectrophotometer equipped with a near infrared detector to generate emission intensity measurements and illustrated them as a topography of intensities for a matrix of excitation wavelengths and emission wavelengths. More particularly, Bachilo et al. described a technique in which photon energies $\lambda_{22}$ and $\lambda_{11}$ are measured over a range of excitation and emission wavelengths, and peaks in the emissions are identified for use in the above equations to solve for diameter and chirality. These peaks may be visualized as three-dimensional surface with peaks defining emission peaks, and valleys between and on the sides of the peaks.

As shown by Bachilo et al, however, the observed correlations do not fit the predictions of the above equations robustly. A more thorough model parameterization was invoked to take into consideration the chirality and other structural features of the SWCNTs species and families.

The general conclusion accepted by most authorities today is that the best fitting relationships between $\lambda_{11}$ and $\lambda_{22}$ are described using the following model equation system where the frequencies of the optical transitions in reciprocal centimeters are:

$$v_{11} = \frac{1 \times 10^7 \text{cm}^{-1}}{157 + 1066.9 d_t} + \frac{A_1 \cos(3\alpha)}{d_t^2} \quad (1)$$

$$v_{22} = \frac{1 \times 10^7 \text{cm}^{-1}}{145.6 + 575.7 d_t} + \frac{A_2 \cos(3\alpha)}{d_t^2} \quad (2)$$

where $\alpha$ is the chirality angle and $A_1$ and $A_2$ are specific constants (710 cm$^{-1}$ and 369 cm$^{-1}$, respectively) referring to families of SWCNTs related by parallels in their n and m coordinates, and where:

$$v_{11} \text{ cm}^{-1} = (1/\lambda_{11} \text{ nm} * 10^7 \text{ nm/cm}) \quad (3)$$

and $$v_{22} \text{ cm}^{-1} = (1/\lambda_{22} \text{ nm} * 10^7 \text{ nm/cm}) \quad (4)$$

In theory, one could measure the absorption and emission matrices of SWCNT mixtures and use the above equations to determine the diameter and chirality of SWCNTs in a given mixture after the peak excitation-emission coordinates have been observed. This is done by simultaneously solving equations (1) and (2) for $d_t$ and $\alpha$ and substituting values for $v_{11}$ and $v_{22}$ calculated using equations (3) and (4).

SUMMARY OF THE INVENTION

The product of the algorithm is typically a three dimensional surface topography of fluorescence intensity as a function of both absorbance (excitation) and fluorescence (emission) wavelengths. The algorithm predicts the fluorescence intensity at any given excitation-emission wavelength coordinate ($\lambda_x, \lambda_m$) for any given mixture of fluorophores.

The double-convolution surface simulation algorithm is derived as follows for a typical excitation-emission matrix experimental data set:

1) First the intensity $I(\lambda_x)_i$ is defined analytically as a function of the excitation wavelength axis value from $\lambda_x$=0 nm to $\lambda_x$=∞ nm for a given emission band i . . . n using any spectral lineshape function, in the following example a Gaussian amplitude equations are used for simplicity:

$$I(\lambda_x)_i = A_{xyi} \cdot \exp[-0.5((\lambda_x - \lambda_{xci})/\lambda_{xwi})]^2 \quad (5)$$

Where for band i $A_{xyi}$ is the amplitude, $\lambda_x$ is the excitation wavelength coordinate, $\lambda_{xci}$ is the excitation wavelength center coordinate and $\lambda_{xwi}$ is the standard deviation. The band coordinates can be represented in units of wavenumbers or wavelength.

2) The intensity as a function of the emission wavelength axis $I(\lambda_m)_i$ is then defined analytically as a function of the emission wavelength axis from $\lambda_m$=0 nm to $\lambda_m$=∞ nm for a given emission band i . . . n:

$$I(\lambda_m)_i = A_{xyi} \cdot \exp[-0.5((\lambda_m - \lambda_{mci})/\lambda_{mwi})]^2 \quad (6)$$

where for band i $A_{xyi}$ is the amplitude of the emission band i, $\lambda_m$ is the emission wavelength coordinate, $\lambda_{mci}$ is the emission wavelength center coordinate and $\lambda_{mwi}$ is the standard deviation.

3) The $I(\lambda_x)_i$ and $I(\lambda_m)_i$ functions are convolved in order to predict the intensity at any given excitation-emission wavelength coordinate to form a three dimensional surface defined by the following double-convolution integral:

$$I(\lambda_x \lambda_m)_i = \int_{\lambda_x = o_{nm}}^{\lambda_x = \infty_{nm}} \int_{\lambda_m = o_{nm}}^{\lambda_m = \infty_{nm}} I(\lambda_x)_i \cdot I(\lambda_m)_i d\lambda_x d\lambda_m \quad (7)$$

The double-convolution in step 2 above can be written more compactly as:

$$I(\lambda_x \lambda_m)_i = I(\lambda_x)_i \otimes I(\lambda_m)_i \quad (8)$$

4) The model further involves the summation of the contributions for all emission bands i . . . n plus any possible background contribution at each possible excitation-emission coordinate. This summation is represented as follows to predict the intensity any given excitation-emission wavelength coordinate:

$$I_{tot}(\lambda_x \lambda_m) = \sum_{i=0}^{n} I(\lambda_x \lambda_m)_i + B(\lambda_x \lambda_m) \quad (9)$$

5) In principle the double-convolution algorithm can also be applied to simulate a three dimensional surface where a kinetic axis may be substituted for either the emission or excitation wavelength axis. That is one may simulate the spectral surface of the fluorescence emission (or absorbance) spectral axes as a function of time such as may be obtained with a Multichannel chromatographic detection technique.

In this case the double-convolution would be represented as:

$$I(\lambda_m t)_i = I(\lambda_m)_i \otimes I(t)_i \quad (10)$$

To predict the absorbance or emission intensity at any wavelength value represented by $(\lambda_m)$ and any time value t. Here $I(t)_i$ may be any kinetic function predicted over any definite or indefinite integral.

The inventive method for identification of a material by analysis of a sample of the material comprises illuminating the sample to be identified with excitation light at a plurality of excitation wavelengths. The intensity of light emitted is measured at a plurality of emission wavelengths for excitation light at each of the plurality of excitation wavelengths to define a measured three-dimensional intensity contour. The measured three dimensional intensity contour is substantially continuous. The values of maxima are located in the three-dimensional intensity contour. The maximum values are compared to a library of values of known maxima associated with known species to obtain a likely more precise identification of a likely maxima. A model of a three-dimensional intensity contour is generated based on maxima values comprising values of likely maxima from the library. The model of the three-dimensional intensity contour is compared to the measured three-dimensional contour to determine residual errors. If residual errors are low enough, the species associated with the maxima values used to generate the model are output as an indicator of species. On the other hand, if residual errors are not low enough, corrections to the model of a three-dimensional intensity contour are determined and used to generate a corrected model of a three-dimensional intensity contour. After that the system returns to the comparison step to test the corrected model.

More particularly, in accordance with the invention, the three-dimensional intensity contour may be associated with points in a matrix on the emission/excitation axes. The model may be generated by calculating, for each intensity maxima and for each point on the emission/excitation matrix, using a computer, a two-dimensional Gaussian (or other appropriate) functions based on measured and/or library maxima for both emission wavelengths as a function of an excitation wavelength and for excitation wavelengths as a function of an emission wavelength. The Gaussian functions may be normalized to form a pair of cylindrical Gaussian surfaces, and the pair of cylindrical Gaussian surfaces are then multiplied by each other to form a three-dimensional Gaussian surface.

Optionally, the illumination of the sample is achieved by setting the output of an illumination source at a particular illumination wavelength and scanning a range of emission wavelengths to detect emitted light emitted by the sample.

Optionally, the setting and the scanning are performed at a plurality of incremental wavelengths.

In accordance with the invention, the locating the values of maxima in the three-dimensional intensity contour may be performed by differentiating the measured three dimensional intensity contour The values associated with a particular maxima may comprise an emission peak center wavelength, standard deviation and amplitude.

In accordance with one particularly preferred example of the invention, the system is used to identify carbon nanotube species and the library comprises data respecting carbon nanotube species.

Optionally, measured maxima may be used to generate the model where no likely identification can be made with a value in the library, or come in the alternative, one of several closest library values used.

BRIEF DESCRIPTION OF THE DRAWINGS

The advantages, and an example method and apparatus for implementing the present invention will be understood from the following description taken together with the drawings, in which:

FIG. 4 illustrates a typical emission characteristic;

FIG. 5 outlines an example result for a mixture of SWCNTs where the nanotube diameter $d_t$ is plotted as a function of both wavelength and chirality angle for SWCNT species in related n-m families;

FIG. 7 illustrates a normalized three-dimensional convolution of emissions for a fixed excitation wavelength in the calculation of the Gaussian distribution for a single point to be used in a second convolution calculation;

FIG. 8 illustrates a normalized three-dimensional convolution of excitation wavelengths for a fixed emission wavelength in the calculation of the Gaussian distribution for a single point to be used in a second convolution calculation;

FIG. 9 is a graphical representation of the function illustrated in FIG. 7 multiplied by the function illustrated in FIG. 8 on a point by point basis;

FIG. 10 is a data map; and

FIG. 11 is a modelled data map.

DETAILED DESCRIPTION OF THE PREFERRED EMBODIMENTS

Figure 1:
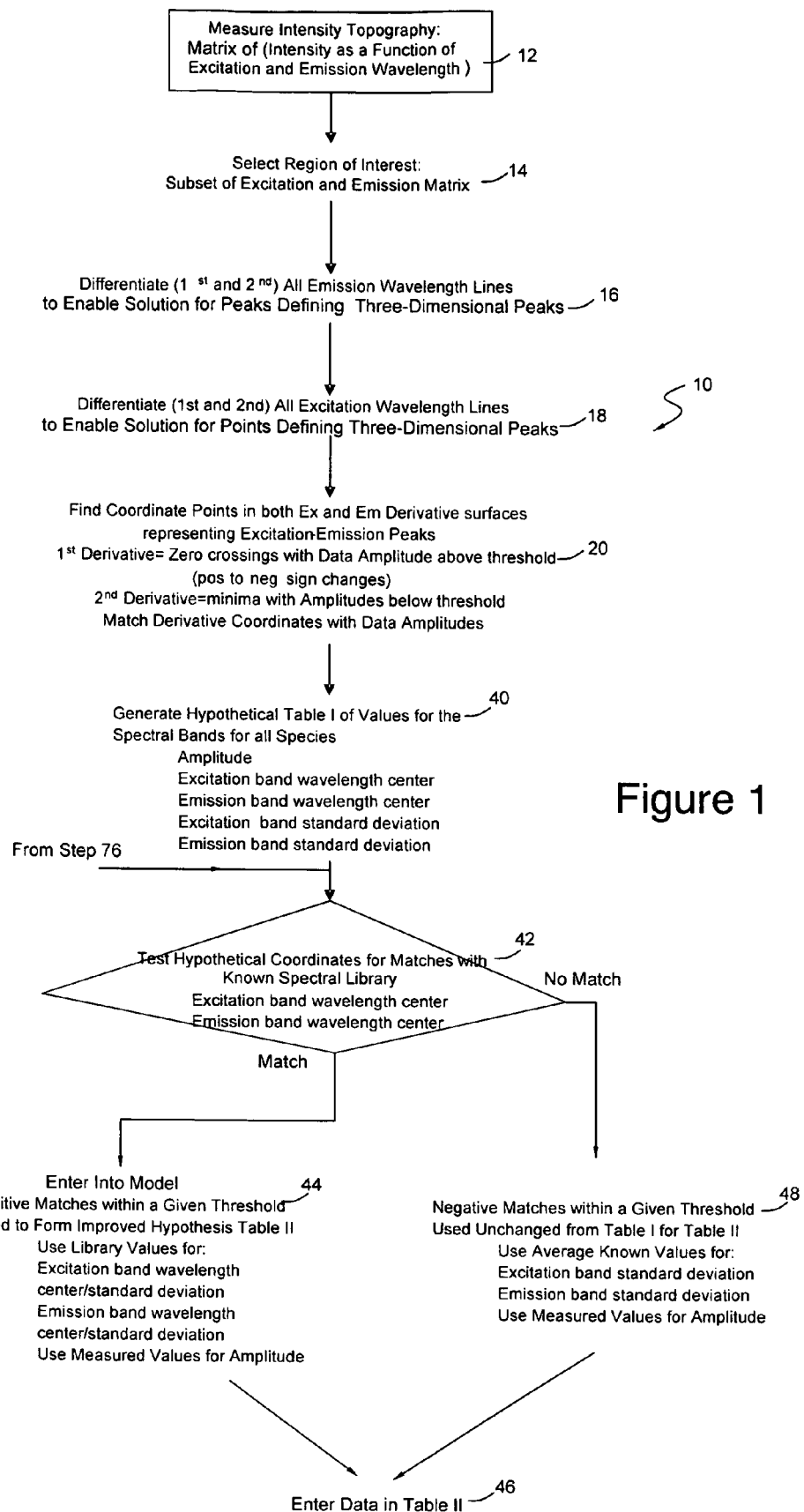
FIG. 1 is a flow diagram illustrating the first phase in the generation of a model of the emission characteristic of a material under study.
Figure 2:
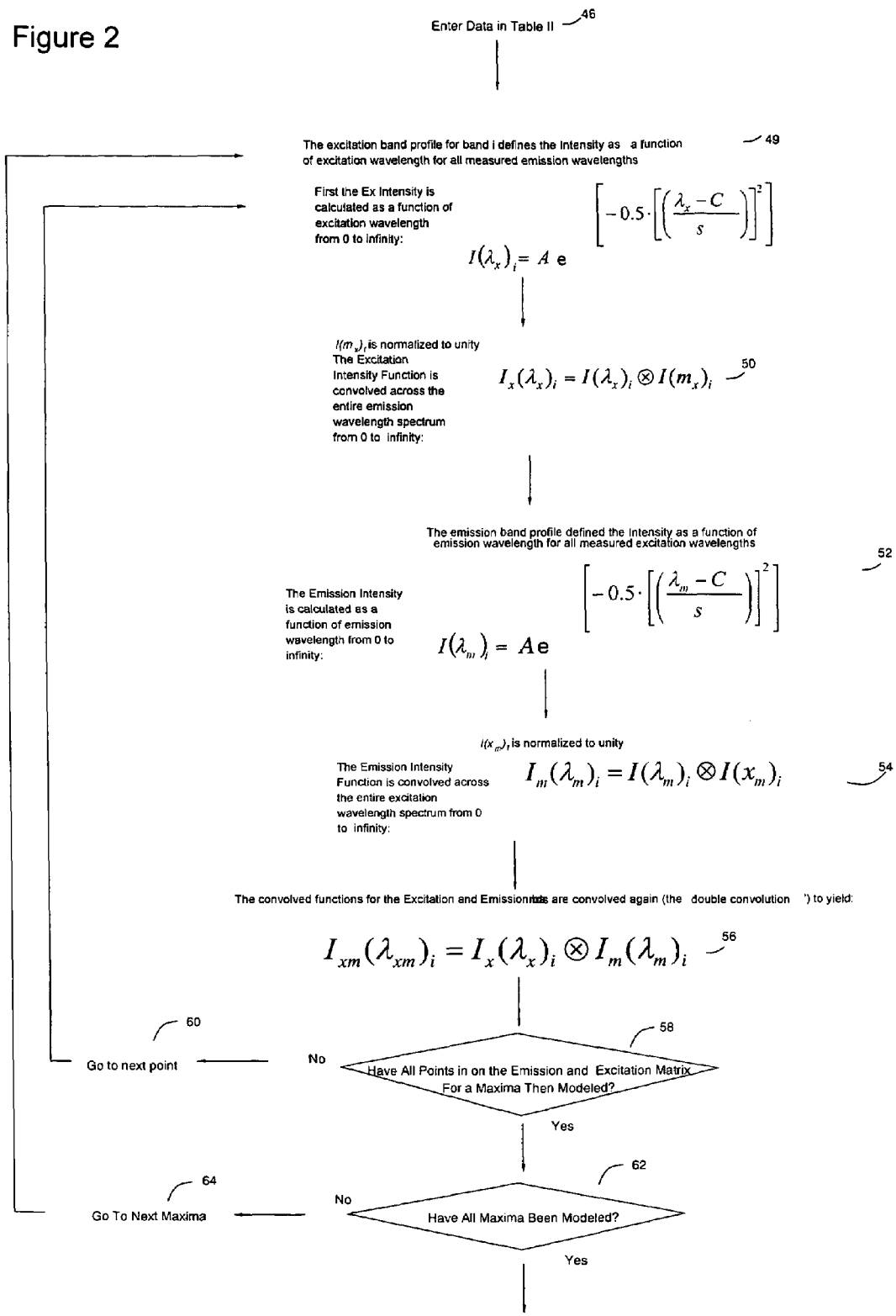
FIG. 2 is a flow diagram illustrating a second phase in the generation of a model of the emission characteristic of a material under study.
Figure 3:
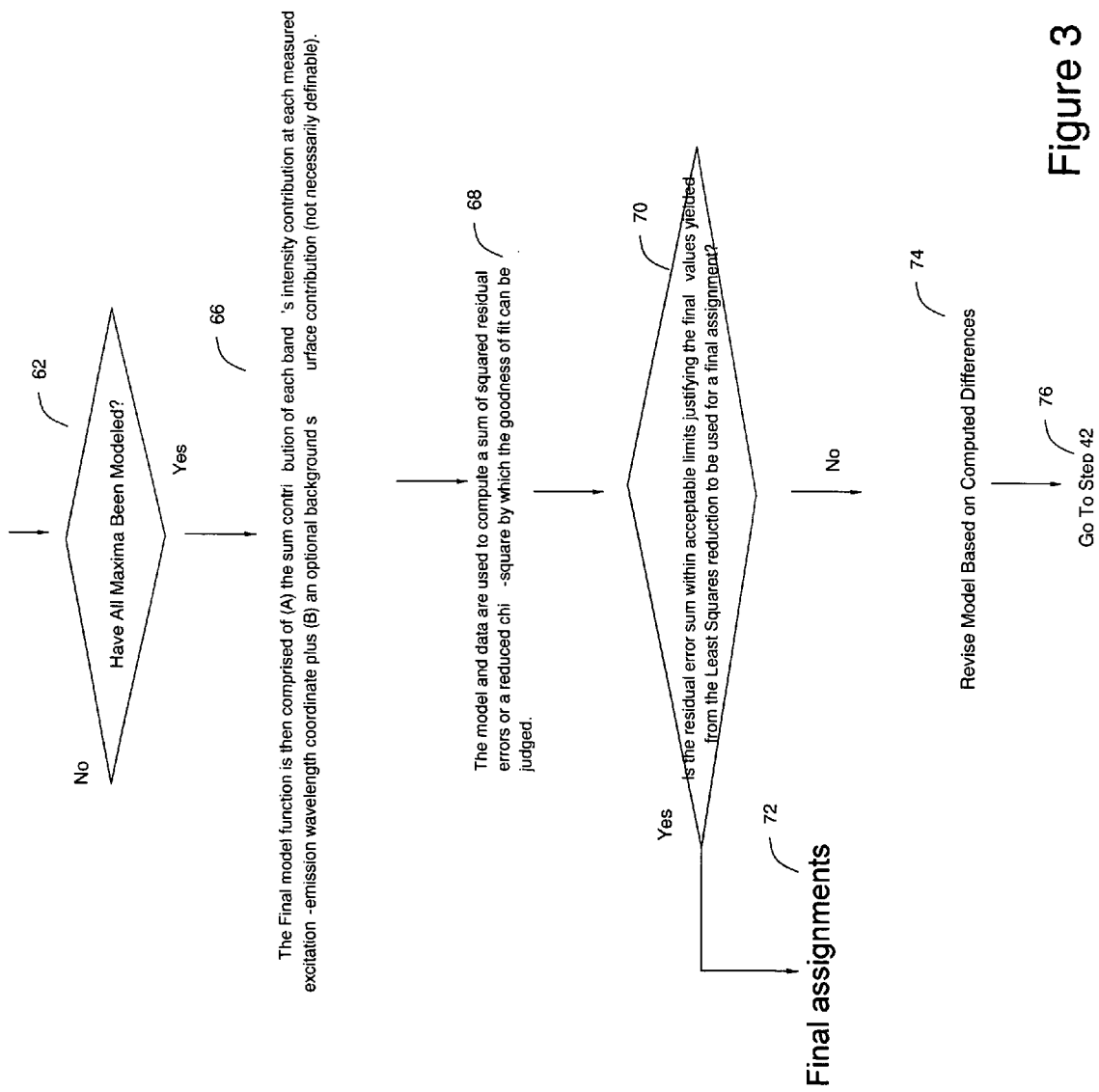
FIG. 3 is a flow diagram illustrating the third phase in the generation of a model of the emission characteristic of a material under study.

The invention relates to a method for an improved analysis designed to classify and to identify materials, and which is particularly useful to classify carbon nanotubes by size and chirality. More particularly, as illustrated in FIGS. 1-3, and in particular FIG. 1, the instant invention is directed to a method 10 incorporating a computer program based on a double spectral convolution algorithm designed to simultaneously, and robustly resolve and identify both the $\lambda_{22}$ and $\lambda_{11}$ optical transitions in materials to be identified, such as single walled carbon nanotube mixtures. For purposes of illustration, the inventive method will be described in connection with its use for the purpose of classifying carbon nanotubes (or mixtures of carbon nanotubes) by their diameter and chirality characteristics.

Generally, the process is begun by taking a sample of the material and putting it into a fluoroscopic measurement device. At step 12, an instrument, such as the HORIBA Jobin Yvon Fluorolog spectrophotometer, used to measure optical transition energies such as $\lambda_{11}$, (the energy emitted at a particular wavelength) in response to an excitation by a photon with an energy $\lambda_{22}$, may be programmed to cause the light output from its light source, for example an xenon lamp, after falling on a planar grating to pass through an entrance slit which acts as a spatial filter having a width sufficient to pass a particular range of wavelengths. The relative position between the grating and the slit can be varied to scan a range of wavelengths. This may be done, for example, by rotation of the planar grating. The light output by the entrance slit thus constitutes an excitation source whose wavelength may be varied, starting, for example, at the lowest wavelength output by the system and progressing to the highest wavelength output by the system. The frequency content (or wavelength content) of the light output by the entrance slit is a function of the width of the slit, but in accordance with the invention, can be characterized as being substantially monochromatic.

In similar fashion the light emitted by the sample under examination may be caused to fall upon a diffraction grating which is rotated relative to a fixed output slit which provides a substantially monochromatic output, thus filtering the output emission signal and outputting a signal in which emission wavelength intensity varies over time.

Preferably the light emitted by the sample under examination may be caused to fall upon a spectrograph grating which is rotated relative to a fixed output slit and provides a substantially polyochromatic output, preferably encompassing the entire spectral output of the sample. The spectrograph outputs a signal in which the emission wavelength intensity varies over a spatial regime covering the sensitive potion of a Multichannel Array Detector affording instantaneous spectral recording of the emission signal. For SWNTs typically one would employ a HORIBA JobinYvon InGaAs array detector (sensitive from 800 nm to 1700 nm); the emission signal would be divided by a reference signal sensitive to the spectral output of the xenon lamp.

In accordance with the invention, this emission readings are done for a first excitation wavelength, thus showing the emission characteristic as a function of emission wavelength for the sample in response to said first excitation wavelength.

When the light output by the entrance slit, at a particular wavelength, is caused to fall on a sample whose characteristics are to be determined, the sample being illuminated by this optical excitation signal will produce an emission signal with an energy $\lambda_{11}$. As a function of time (or space in the case of an MCA), $\lambda_{11}$ will vary as a function of the product of the bandpass characteristics of the slit and the fluorescence emission response characteristic of the material under examination for that excitation wavelength.

Accordingly, a two-dimensional characteristic, for example emission wavelength intensity for a particular excitation wavelength, may be modeled using a mathematical function known as a convolution or faltung. This model can be extended by multiple two-dimensional characteristics to generate a three-dimensional model. Such modeling, as is explained below, may be based on preliminary evaluation of the emission output for a single excitation wavelength. The model may then be compared to the actual reading and adjusted until a good match is achieved between the model and the actual reading. The parameters used to generate the model are then output as an indication of the characteristics of the material under examination.

In accordance with the invention, the excitation wavelength is also incremented from the first excitation wavelength to a second excitation wavelength and the emissions from the sample are scanned to determine the characteristic with respect to the second excitation wavelength. This process is repeated, successively incrementing the excitation wavelength to generate the three-dimensional characteristic (FIG. 4) giving emission intensity for a range of excitation and emission wavelengths.

More particularly, as illustrated in FIG. 1, after the topography of intensity has been generated for the points on the $\lambda_{11}$ (emission) and $\lambda_{22}$ (excitation) matrix that step 12, a region of interest is selected at step 14 based on those areas of the matrix which exhibit values characteristic of a signal constituting an emission peak. In many cases, this may be the entire matrix (such as the matrix illustrated in FIG. 4), particularly where the carbon nanotubes have characteristics which are within an expected range of characteristics.

Once the matrix illustrated in FIG. 4 has been identified, the raw data must be used to identify emission peaks which correspond to particular nanotube species. This information is then correlated with theoretical data specific to particular nanotube species emissions in order to generate a theoretical model which may be compared to the actual reading to provide an indication of the acceptability of the actual reading or drive downstream iterations of the original model generated from the raw data to iteratively approach a theoretical model which is within an acceptable range of the raw data, and thus exhibits a desired degree of goodness of fit. Such iterative testing on successive models may be conducted by either generating proposed-changes to the theoretical model based on the difference between the theoretical model and the raw data and/or by iterative arbitrary adjustments of the data, testing of those arbitrary adjustments, and repeating that process (guided by the results obtained during comparison of the prior model or models) until an acceptable match is achieved. Several ways of performing this process will be discussed in detail below.

More particularly, the data illustrated, by way of example, in FIG. 4 includes a number of visible peaks which should correspond to particular nanotube species.

Peaks may be detected mathematically by differentiation of the three-dimensional matrix illustrated in FIG. 4. The three-dimensional topography illustrated in FIG. 4 also may include a number of hidden peaks, which may be detected by taking the second derivative of the data illustrated in FIG. 4. Such differentiation and processing of the waveforms may take advantage of techniques that are used in conventional strictly two-dimensional fluoroscopic systems as are shown in, for example, Inczyédy J, Lengycl Y, Ure AM (eds), (1997) Compendium of Analytical Nomenclature, International Union of Pure and Applied Chemistry, $3^{rd}$ Ed.

The topography illustrated in FIG. 4 also illustrates a signal which for a given emission wavelength will show the characteristic of the material under examination for a range of excitation wavelengths. It is noted that, in accordance with the invention, a real signal for a given emission wavelength being excited by a range of excitation wavelengths by scanning the grating which varies the wavelength of the excitation source may be generated. However, this would be duplicative of the first scan using fixed excitation wavelengths. The first scan allows the generation of a virtual signal showing the emission response as a function of wavelength for a fixed excitation wavelength for the sample material under analysis. This is due to the virtually instantaneous response time of the optics portions of optical systems as compared to mechanical scanning systems.

The absorption transition function predicts the photon emission intensity as a function of excitation-emission wavelength coordinates for any given SWCNT species i . . . n. Importantly, the intensity and wavelength coordinates can be described by any appropriate analytical spectral lineshape function, in this case a Gaussian amplitude equation is used as described below.

The intensity of the emission transition $\lambda_{11}$ for $SWCNT_i$ as a function of wavelength is, $$I\lambda_{11}(\lambda)_i = A_{xyi} * \exp[-0.5 * ((\lambda_m - \lambda_{11ci})/\lambda_{11iw})]^2 \quad (11)$$

where $A_{xyi}$ is the 'double convolved' amplitude parameter linking the emission and excitation coordinate equations, $\lambda_m$ is the observed emission wavelength, $\lambda_{11ci}$ is the maximum emission transition intensity wavelength and $\lambda_{11iw}$ is the spectral lineshape width (standard deviation). Note this equation is defined specifically for carbon nanotube analysis and equivalent to Eq. 6.

Likewise, the intensity of the excitation transition $\lambda_{22}$ for $SWCNT_i$ as a function of wavelength is defined equivalent to Eq. 5 as, $$I\lambda_{22}(\lambda)_i = A_{xyi} * \exp[-0.5 * ((\lambda_x - \lambda_{22ci})/\lambda_{22w})]^2 \quad (12)$$

where, $A_{xyi}$ is defined for Eq. 11 and the lineshape width and center functions are likewise self explanatory.

The double convolution is represented for each SWCNT species i . . . n equivalent to Eq 8 as follows:

$$SWCNT_i = I\lambda_{11}(\lambda)_i \otimes I\lambda_{22}(\lambda)_i \quad (13)$$

In practice, this is achieved by multiplying the predicted intensity values from Eq. 11 and Eq. 12 at each excitation-emission wavelength coordinate in the spectral region of interest.

The model for any given mixture includes the sum of the intensity contributions for all the SWCNT species i . . . n at each resolved excitation-emission coordinate in the spectral region of interest. Moreover, the model includes provisions for background components to the intensity surface in the region of interest. Hence the overall model can be summed at each excitation-emission wavelength coordinate equivalent to Eq. 9 as follows:

$$SWCNT_{all} = \sum_{i=1}^{n} SWCNT_i + C \quad (14)$$

Where C represents any hypothetical function describing the background intensity contribution.

For the various carbon nanotube species the theoretical emissions may be mapped as illustrated in FIG. 5. Likewise, relative amplitude between these emissions, and the standard deviation of the emissions may also be calculated. All of this calculated theoretical data may then be input into a data library for reference by a computer during generation of the initial model.

As alluded to above, it is imperative to identify the obvious peaks (true maxima) and the hidden peaks (inflections) for each scan in the emission axis of the topography illustrated in FIG. 4. This may be done, at step 16, by differentiating the emission intensity function defined by a "line" of the topography of intensity generated for the points on the $\lambda_{11}$ (emission) axis for a fixed excitation wavelength. The zeros in this intensity function further defined by a sign change from negative to positive with increasing emission wavelengths correspond to peaks in the emission data surface. The first derivatives are computed as the least squares slope ($dF/d\lambda$) in user selectable windows (i.e., 3, 5, 7 or 9 measured intervals) which can be chosen to optimize peak sensitivity and progressively dampen and or exclude background noise contributions. The Peak identity trigger mechanism is further constrained by a threshold parameter in percent (between 0 and 100%) of the maximal amplitude observed in the data surface; this threshold serves to eliminate background noise contributions.

The second derivative of the emission intensity function can also be taken at step 16. The existence of a minimal value in the twice differentiated waveform below a certain threshold may indicate a hidden peak. A hidden peak may be caused by a number of phenomena, such as two peaks which are very close to each other and most often when a narrow peak is obscured by a taller broader peak. As with the first derivative, the second derivative can be computed as the least squares slope(s) over user defined intervals to dampen noise contributions and increase spectral resolution. The second derivative threshold is also constrained between (0 to 100%) determined by taking into account the minimum amplitude of the second derivate surface.

As noted above, any techniques used in the art for working with a conventional fluoroscopic output may also be used to determine the existence of peaks and hidden peaks.

The above process is repeated computationally for each line of intensity information for all successive emission wavelengths.

In addition, in order to identify the peaks and the hidden peaks for each scan in the excitation intensity axis of the topography illustrated in FIG. 4, at step 18, one similar to Step 16, the first and second derivatives along the $\lambda_{22}$ (excitation) axis for a fixed emission wavelength.

The above process is repeated computationally for each line of excitation intensity information for successive emission wavelengths until the entire intensity topography has been processed.

Figure 6:
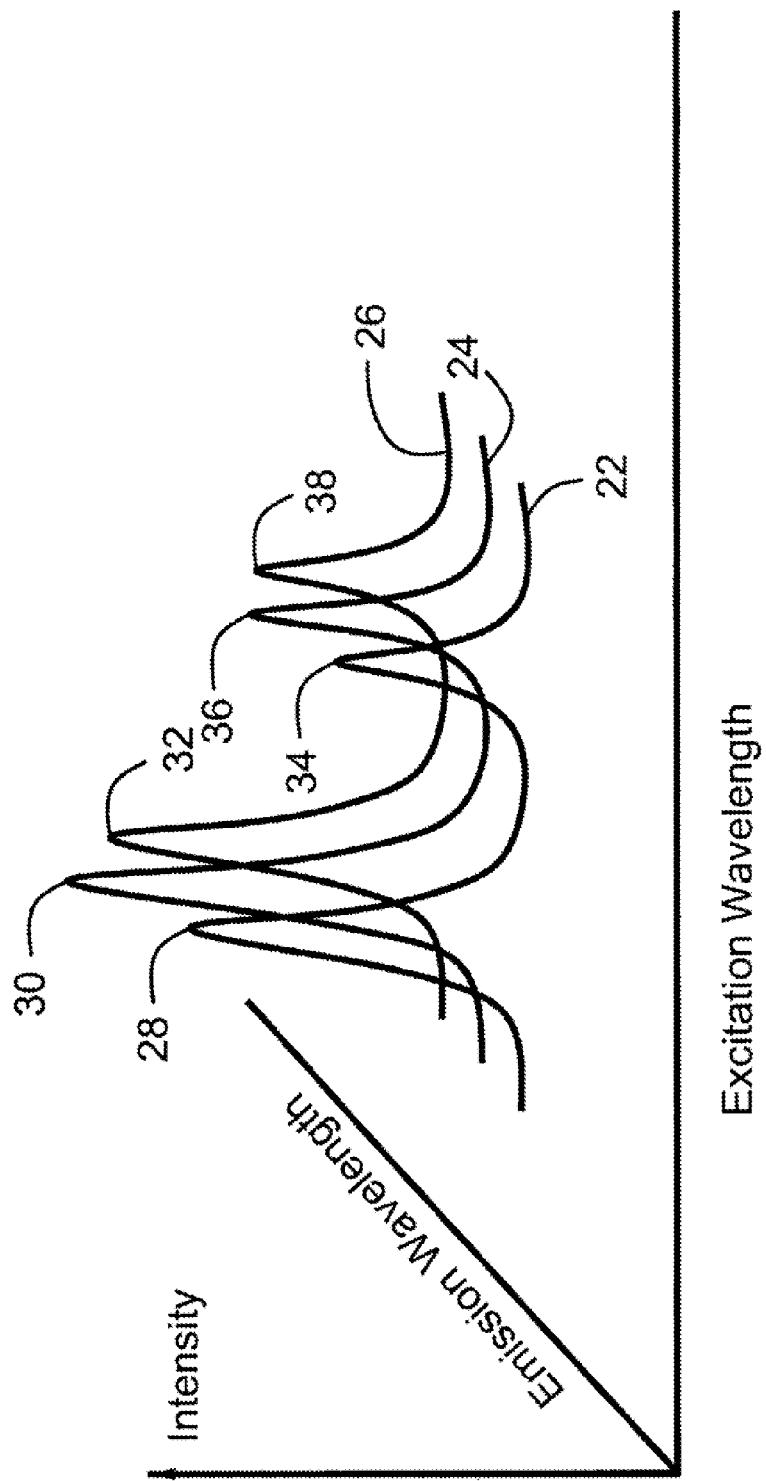
FIG. 6 illustrates the use of a plurality of readings to determine a maxima point in three dimensions.

Referring to FIG. 6, at step 20, successive waveforms for emission intensity, for example waveforms 22, 24 and 26, each for its respective fixed excitation wavelength define a plurality of peaks. Certain of these peaks, for example peaks 28, 30 and 32, define a substantially continuous function corresponding to a constant emission wavelength. As can be seen in FIG. 6, the peaks in this defined substantially continuous function correspond to three-dimensional topographic peaks, for example the one at peak 30.

Likewise, peaks 34, 36 and 38 define a second substantially continuous function corresponding to a different constant emission wavelength. Peaks in the second substantially continuous function corresponding to the different constant emission wavelength, in turn, define three-dimensional topographic peaks, in this case the one at peak 36.

At step 40, the measured amplitude in the raw topographical information is associated with an excitation band wavelength center (obtained as described above in Step 18), an emission band wavelength center (also obtained as described above in Step 16). a standard deviation associated with the waveform corresponding to a fixed excitation wavelength, such as waveform 30, and a standard deviation associated with the substantially continuous function corresponding to a constant emission wavelength.

Once the peak excitation and emission coordinates are indentified one can compute the apparent full-width-half-maxima (FWHM) for each peak in both the excitation and emission axes. The FWHMs can then be used to compute the standard deviation of the peak in both excitation-emission directions as related to Eqs. 11 and 12. The FWHMs are computed for each peak using a bi-drectional search vector twice, once for the excitation and once for the emission axes. The peak coordinate value is marked as an origin and the amplitude of the data is evaluated at each measured interval (above and below) the peak coordinate until the amplitude is less than or equal 0.5 times the peak. The closest coordinates less than or equal 0.5times the peak are used to compute the FWHM and then the standard deviation. The FWHM search routine cannot evaluate overlapping peaks and the search routine also calculated the mean, median and mode values for all the observed widths.

As described above standard deviations (widths) can be calculated from the raw topographical intensity information. This is done for each peak in the intensity in the raw data which forms the topographic intensity map illustrated in FIG. 4. This data is written into Table I. In principle, in the absence of complications, the raw data would be the final data and would be used to determine which nanotube species are in the sample.

However, as alluded to above, complicating factors, such as emission peaks which are close to each other, background noise, instrument inaccuracy, and the like are likely to make the decoding of the species information in the intensity topography a less than straightforward procedure. Accordingly, in accordance with the invention and as more fully appears below, the data is interpreted, a model is determined based on that interpretation and the model is tested and improved in an iterative fashion until an acceptable degree of fit is achieved between the theoretical model and the actual raw data. At that point the nature of the nanotube species and their relative concentrations, as were used to generate the model, may be output as an indicator of actual nanotube species and their relative concentrations in the sample.

At step 42, the raw data intensities (which are proportional to relative concentrations of various nanotube species) are taken together with measured standard deviations, peak emission wavelengths and peak excitation wavelengths, and compared as a set to a library of known intensity, and known deviation and wavelength characteristics of nanotube species.

If the comparison of the experimentally measured peaks correlates to known nanotube species, the known species is identified at step 42.

At step 44, positive matches within an acceptable degree of error are identified and, at step 46, entered into a database (table II) which is to be used to generate the model.

Where there is no match for a peak measured experimentally as compared to the library of emission peaks as determined at step 48, within an acceptable degree of error, the assumption is made that modeling on that point cannot be reliably based on library information, and the raw data is used in the model to be based on Table II and this information entered into Table II at step 46. Thus, the final model comprises raw data where no match in the library can be found, and library values substituted for the raw data where a match can be found, with the intensity of all peaks scaled proportionally to the raw data. The Table II data is then used to model the emission topography.

Referring to FIG. 2, modeling of the emission topography comprises modeling emission intensity for each point on the $\lambda_{11}$ (emission) and $\lambda_{22}$ (excitation) matrix. While each point on the topography represents a finite two-dimensional projection on the $\lambda_{11}$ (emission) and $\lambda_{22}$ (excitation) matrix of the intensity, modeling of a single point may be performed by first modeling the excitation band profile. This is done at step 49 by modeling intensity over a range of emission wavelengths for a fixed excitation wavelength. In particular, excitation intensity is calculated as a function of excitation wavelength from zero to infinity. A Gaussian distribution is a good approximation of typical fluoroscopic readings and one may calculate values using Eq. 11

$$I\lambda_{11}(\lambda)_i = A_{xyi} * \exp[-0.5*((\lambda_m - \lambda_{11ci})/\lambda_{11iw})]^2$$

Where $I\lambda_{11}(\lambda)_i$ is the intensity at a particular emission wavelength, $A_{xyi}$ is the square root of the raw data amplitude ($A^{1/2}$) measured by the instrument and reported as raw data in Table II, $\lambda_{11iw}$ is either the raw measured or library standard deviation, $\lambda_m$ is the emission wavelength at which fluorescence emission function is being evaulated, exp is the natural log base typically used in the expression of a Gaussian distribution, and $\lambda_{11ci}$ is the library or raw data value used in Table II as the center wavelength of emission.

As can be seen from inspection of equation (11), the result is a two-dimensional Gaussian distribution. This Gaussian distribution may be projected in three dimensions to define a Gaussian planar surface as illustrated in FIG. 7. This "normalization" is performed at step 50. The step is represented by the equation 13 as follows:

$$SWCNT_i = I\lambda_{11}(\lambda)_i \odot I\lambda_{22}(\lambda)_i \qquad (13)$$

where $I\lambda_{22}(\lambda)_i$ is assumed to be unity for every point in the universe of its possible solutions.

At step 52, modeling is continued by modeling intensity over a range of excitation wavelengths for a fixed emission wavelength. In particular, emission intensity is calculated as a function of emission wavelength from zero to infinity. A Gaussian distribution is again a good approximation of expected fluoroscopic readings in accordance with the invention and one may calculate values using the equation 12:

$$I\lambda_{22}(\lambda)_i = A_{xyi} * \exp[-0.5*((\lambda_x - \lambda_{22ci})/\lambda_{22w})]^2$$

Where $I\lambda_{22}(\lambda)_i$ is the intensity at a particular excitation wavelength, $A_{xyi}$ is the square root of the raw data amplitude ($A^{1/2}$) measured by the instrument and reported as raw data in Table II, $\lambda_{22iW}$ is either the raw measured or library standard deviation, $\lambda_x$ is the excitation wavelength at which fluorescence excitation function is being evaulated, exp is the natural log base typically used in the expression of a Gaussian distribution, and $\lambda_{22ci}$ is the library or raw data value used in Table II as the center wavelength of emission.

As can be seen from inspection of equation (12), the result is a two-dimensional Gaussian distribution. This Gaussian distribution may be projected in three dimensions to define a Gaussian planar surface as illustrated in FIG. 8. This "normalization" is performed at step 54. The step is represented by the equation 13:

$$SWCNT_i = I\lambda_{11}(\lambda)_i \otimes I\lambda_{22}(\lambda)_i \qquad (13)$$

where $I\lambda_{11}(\lambda)_i$ is assumed to be unity for every point in the universe of its possible solutions.

At step 56, the intensities at each point on the $\lambda_{11}$ (emission) and $\lambda_{22}$ (excitation) matrix for the function illustrated in FIG. 7 is multiplied by the value of the intensity at the same point on the $\lambda_{11}$ (emission) and $\lambda_{22}$ (excitation) matrix illustrated in FIG. 8. The result of this operation is the generation of a three-dimensional intensity function for a single point on the $\lambda_{11}$ (emission) and $\lambda_{22}$ (excitation) matrix model corresponding to a single point for a single peak in the raw data. This data corresponding to this point is a three-dimensional bell curve, as is illustrated in FIG. 9.

Accordingly, steps 49 through 56 must be repeated for each point in the first maxima in the Table II model. The steps must then be repeated for each maxima. Accordingly, at step 58, the system determines whether additional points need to be calculated for a given maxima, and if the answer to this question is yes the system proceeds to step 62 and returns to step 49. If the answer is no, the system proceeds to step 60.

In similar fashion, at step 62, the system determines whether there are additional maxima to be calculated for the model, and if the answer to this question is no, the system proceeds to step 64 and returns to step 49. If the answer is yes the system proceeds to step 66.

Accordingly, at the end of this series of operations, a three-dimensional set of intensities defining a Gaussian distribution in three dimensions for the intensity at each point on the $\lambda_{11}$ (emission) and $\lambda_{22}$ (excitation) matrix, and for each emission peak is defined. For example, if the $\lambda_{11}/\lambda_{22}$ matrix is a 500 by 500 matrix, there would be 25,000 coordinate points and 1,000 three-dimensional Gaussian distributions such as that illustrated in FIG. 9 for each intensity peak in the model. Continuing the example, if that were ten intensity peaks representing ten nanotube species, there would be 10,000 three-dimensional Gaussian distributions as illustrated in FIG. 9.

In accordance with the invention, for each point on the $\lambda_{11}/\lambda_{22}$ matrix, the intensity contributions of the three-dimensional Gaussians, such as that illustrated in FIG. 9 are added together to obtain a total value for modeled intensity for that point. As will be described below, the model is tested by taking the total intensity for each point and comparing it to the raw value directly measured by the instrument, as more fully appears below.

Each three dimensional Gaussian distribution peak as in FIG. 9 can be simulated with 5 parameters, 1) the amplitude, 2) the emission center, 3) the emission standard deviation, 4) the excitation center and 5) the excitation standard deviation. Hence for 10 peaks one requires 50 model parameters for any size of $\lambda_{11}/\lambda_{22}$ matrix. This is in stark contrast to the number of parameters needed to fit each of the 10,000 bell curves separately; if each excitation bell curve on both the excitation and emission axes requires 3 parameters then one would potentially invoke 30,000 fitting parameters. Hence the 'double convolution' invention reduces the number of fitting parameter by a factor of 30,000/50=600. Larger relative parameter reduction factors can be achieved from 1) using larger numbers of measured intervals, 2) use of known or fixed Library model parameters or 3) other 'analytical targeting' for the formulaic parameterization with the double convolution equation system as explained above.

If it is determined at step 62 that all maxima have been modeled, the system proceeds to step 66, where all intensity contributions are added together for all points on the $\lambda_{11}/\lambda_{22}$ matrix. In addition, background noise and other model components as are used in conventional fluoroscopic systems may also be added into the model, although the same may not be precisely known.

At step 68 the modeled values are compared to the raw data values, after the modeled values have been normalized for a total intensity and energy equal to that of the raw data. More particularly, the model and the raw data are used to compute a sum of squared residual errors or a reduced chi square by which the goodness of fit can be judged. If the errors are within acceptable limits, at step 70 the parameters which generate the model are output as the final assignments at step 72. If they are not, the system proceeds with a first iteration from the initial parameters to the second iteration parameters. The model may be better understood by recognizing that the model data may be illustrated as an intensity shades of gray display, as shown in FIG. 10. Similarly, the model would take the form of the representation illustrated in FIG. 11.

At step 74, the differences between the raw data and the model are analyzed using any one on a variety of techniques in order to derive information which may be used to improve the model. For example, the difference between the model and the raw data may indicate the species which have been neglected. Such a condition may appear as negative peaks in the data. The differences may also indicate differences in peak values between that peaks in the model and the peaks in the raw data. If these differences cannot be accounted for by such factors as missing peaks or the inability to match a raw data peak with a library peak, this may call for adjustment of the peak value.

A wide range of techniques are possible for the adjustment of the model. For example, if the residual errors found are not within acceptable limits then an assessment may be made for the possibility of under/over parameterization, and peaks are added or deleted in spectral regions of obvious or suspected residual error contribution. The modeled parameters are then optimized using least squares minimization and the assignments underlying the model are checked. In connection with the calculations associated with least squares minimization, the same is computed using a software package sold by Frontline Systems under the trademark Premium Solver Platform and using the large-scale general reduced gradient engine.

Alternatively the model parameters for the excitation and emission wavelength wavelengths may be modeled using the analytical equations of Bachilo et al., where the unknown parameters would be the chirality angle and the tube diameter.

Another alternative is for the integer values for n and m to be used to compute chirality and diameter for each hypothetical tube assignment, using the same model formulation, assessment and assignment protocols.

After the model has been iteratively adjusted, the system proceeds at step 76 to return to step 42 where the system goes to the steps described above, attempting to substitute library values for any raw data which still may remain in the model. The system then proceeds to the various steps described above, testing the iteratively revised model entered into revised Table II. The process is repeated, optionally a limited number of times, until final assignments are output at step 72.

While an illustrative embodiment of the invention has been described, it is understood that various modifications may be made by those of ordinary skill in the art without departing from the spirit and scope of the invention which is limited and defined only by the appended claims.

The invention claimed is:

1. A method for identification of a sample of a material, comprising:
    (a) illuminating a sample to be identified with excitation light at a plurality of excitation wavelengths;
    (b) measuring the intensity of light emitted, at a plurality of emission wavelengths, by said sample for excitation light at each of said plurality of excitation wavelengths to define a measured three-dimensional intensity contour;
    (c) locating the values of maxima in said three-dimensional intensity contour;
    (d) comparing said values of maxima to a library of values of known maxima associated with known species to obtain library maxima;
    (e) generating a model of a three-dimensional intensity contour based on values comprising values to library maxima from said library and values of said measured three-dimensional intensity contour;
    (f) comparing said model of a three-dimensional intensity contour to said measured three-dimensional contour to determine residual errors;
    (g) if residual errors are not low enough, determining corrections to said model of a three-dimensional intensity contour to generate a corrected model of a three-dimensional intensity contour, and returning to said comparison step (f) to test said corrected model; and
    (h) outputting said species associated with said maxima values used to generate said model as an indicator of species.

2. A method as in claim 1, wherein said illumination of said sample is achieved by setting the output of an illumination source at a particular illumination wavelength and scanning a range of emission wavelengths to detect emitted light emitted by said sample.

3. A method as in claim 2, wherein said setting and said scanning are performed at a plurality of incremental wavelengths.

4. A method as in claim 1, wherein said locating the values of maxima in said three-dimensional intensity contour is performed by differentiating said measured three dimensional intensity contour.

5. A method as in claim 1, wherein said library of values of known maxima comprise an emission peak center wavelength, standard deviation and amplitude.

6. A method as in claim 1, wherein said library comprises data respecting carbon nanotube species.

7. A method as in claim 1, wherein said three-dimensional intensity contour is associated with points in a matrix on the emission/excitation axes, and wherein said model is generated by calculating, for each intensity maxima and for each point on the emission/excitation matrix, using a computer, a two-dimensional Gaussian functions based on measured and/or library maxima for emission wavelengths as a function of an excitation wavelength and for excitation wavelengths as a function of an emission wavelength, said Gaussian functions are normalized to form a pair of cylindrical Gaussian surfaces are multiplied by each other to form a three-dimensional Gaussian surface.

* * * * *

UNITED STATES PATENT AND TRADEMARK OFFICE
CERTIFICATE OF CORRECTION

PATENT NO. : 7,569,839 B2
APPLICATION NO. : 11/113961
DATED : August 4, 2009
INVENTOR(S) : Gilmore et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 41 days.

Signed and Sealed this

Seventh Day of September, 2010

David J. Kappos
*Director of the United States Patent and Trademark Office*